United States Patent
Locsin et al.

(10) Patent No.: US 8,398,610 B2
(45) Date of Patent: Mar. 19, 2013

(54) CATHETER WITH DISTENSIBLE AND FRANGIBLE CAP

(75) Inventors: Brent Locsin, San Francisco, CA (US); Barry Wohl, Minneapolis, MN (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 396 days.

(21) Appl. No.: 12/759,192

(22) Filed: Apr. 13, 2010

(65) Prior Publication Data

US 2011/0251589 A1  Oct. 13, 2011

(51) Int. Cl.
- *A61M 25/10* (2006.01)
- *A61M 5/00* (2006.01)
- *A61F 2/84* (2006.01)
- *A61F 2/82* (2006.01)

(52) U.S. Cl. .................. 604/509; 604/508; 604/244
(58) Field of Classification Search ............. 604/509
See application file for complete search history.

(56) References Cited

U.S. PATENT DOCUMENTS

| | | | |
|---|---|---|---|
| 3,995,623 A | | 12/1976 | Blake et al. |
| 4,023,559 A | * | 5/1977 | Gaskell ................ 600/572 |
| 4,946,440 A | * | 8/1990 | Hall ................ 604/164.09 |
| 5,078,681 A | * | 1/1992 | Kawashima .............. 606/198 |
| 5,147,314 A | * | 9/1992 | Vaillancourt .............. 604/158 |
| 5,221,258 A | * | 6/1993 | Shturman ................ 604/97.02 |
| 5,607,466 A | * | 3/1997 | Imbert et al. ............. 623/1.11 |
| 6,743,208 B1 | * | 6/2004 | Coyle ................ 604/164.13 |
| 7,052,510 B1 | * | 5/2006 | Richter ................ 623/1.11 |
| 7,628,306 B2 | | 12/2009 | Spurchise et al. |
| 7,758,624 B2 | * | 7/2010 | Dorn et al. ............. 623/1.11 |
| 2002/0183826 A1 | * | 12/2002 | Dorn et al. ............. 623/1.11 |
| 2005/0148925 A1 | * | 7/2005 | Rottenberg et al. ............. 604/9 |
| 2005/0283221 A1 | * | 12/2005 | Mann et al. ............. 623/1.11 |
| 2007/0073271 A1 | * | 3/2007 | Brucker et al. ............. 604/537 |
| 2007/0225659 A1 | | 9/2007 | Melsheimer |
| 2007/0270930 A1 | * | 11/2007 | Schenck ................ 623/1.11 |
| 2008/0208310 A1 | * | 8/2008 | McDermott et al. ......... 623/1.11 |

* cited by examiner

*Primary Examiner* — Carl H Layno
*Assistant Examiner* — Erin Piateski

(57) ABSTRACT

A catheter for delivering a medical implant in a patient's vasculature includes an elongate catheter having a distensible and frangible cap mounted across the open distal end thereof. The cap is distendable by pressure within the catheter to provide a bumper tip for guiding the catheter through a patient's vasculature. At the desired site for deploying the medical implant, the cap is ruptured to permit the implant to be advanced through the distal opening. Methods of using the catheter are also disclosed.

6 Claims, 3 Drawing Sheets

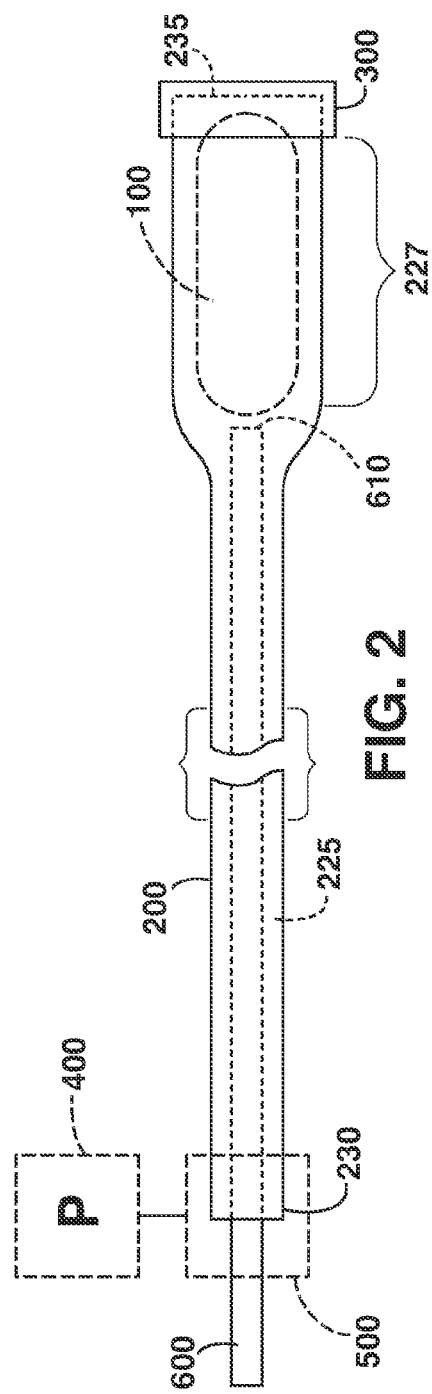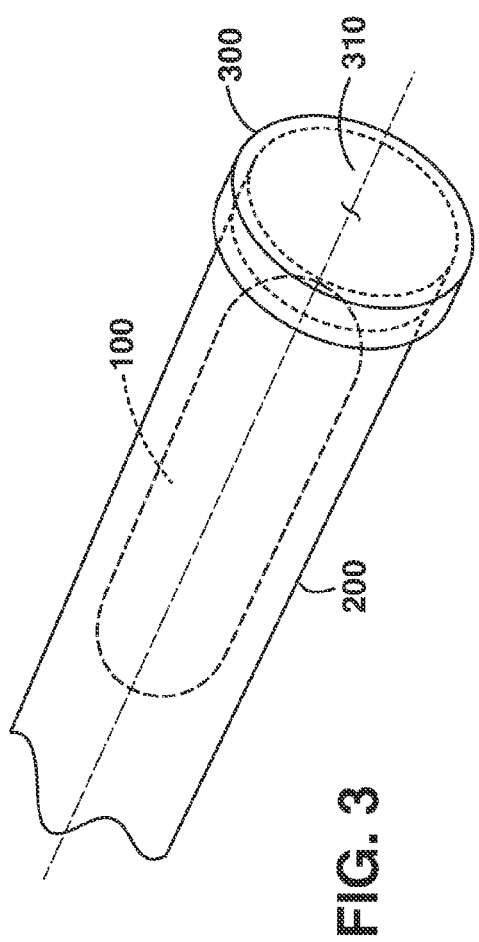

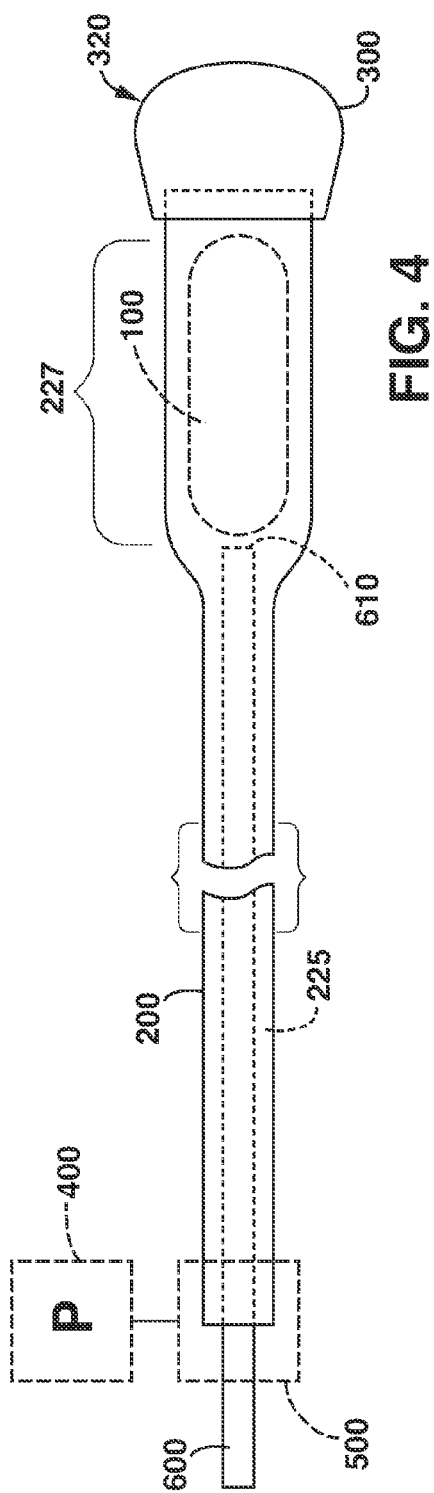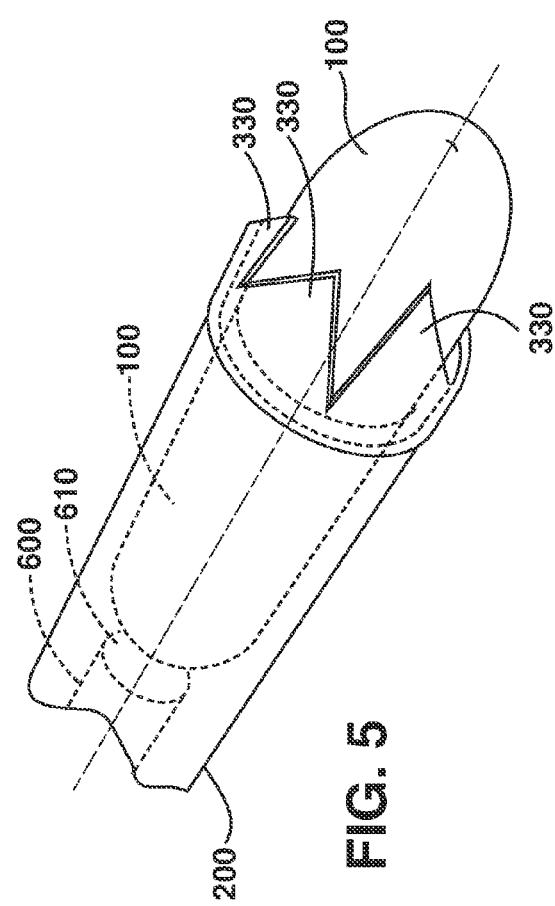

CATHETER WITH DISTENSIBLE AND FRANGIBLE CAP

TECHNICAL FIELD

This invention relates generally to biomedical devices that are used for treating vascular conditions. More specifically, the invention relates to an implant delivery catheter having a type of bumper tip for safely navigating a patient's vascular system.

BACKGROUND OF THE INVENTION

Catheters are commonly used in vascular interventional or diagnostic procedures. The catheter is threaded through the vasculature to a destination and treatment is applied at the destination. The treatment can take many forms, but a common treatment includes stent delivery wherein the stent is collapsible to a reduced profile delivery configuration for traversing the vasculature to the treatment site. Other treatments include the delivery of implantable devices that have a relatively large cross section, and may not be collapsible for convenient transluminal delivery via catheterization. Certain of these uncollapsible devices also may be constructed such that it is undesirable, or difficult, or expensive to provide a passageway through the device to accommodate guidewires or the like to assist in delivery. For example, it may be undesirable to design a battery for a leadless implantable pacemaker with a through-hole to accommodate a guidewire. Embodiments hereof relate to systems and methods for delivering a leadless pacing system, such as leadless medical implants within body tissue, such as tissue of the heart. A leadless medical implant that may be adapted for use in embodiments hereof is a leadless pacing system of the type described in U.S. Pat. No. 5,193,539 to Shulman et al. Generally, such a medical implant includes at least two electrodes and a capsule-shaped housing that hermetically encloses the pacing system's electrical components, including a wireless communication system and an internal power source. When implanted, the leadless pacing system is in electrical contact with heart tissue.

The medical implant described herein is sized to be tracked through the vasculature, i.e., through femoral, jugular, or subclavian blood vessels, within delivery systems hereof and may have a diameter or transverse dimension of up to 9 mm. Medical implants described herein may be delivered through the vasculature to be implanted at a septum of the heart or at the apex of the right ventricle. In other embodiments, medical implants described herein may be implanted within another heart chamber on either side of the heart. Although medical implants described herein are described as leadless pacing systems, in other embodiments hereof delivery and fixation systems and methods herein may be used to deliver and implant other medical devices that are configured to be secured within body tissue, such as a sensor device or another type of stimulator device, which may or may not be "leadless" or self-contained.

When using a catheter system to deliver devices that would otherwise be difficult to deliver, either due to crossing diameter or due to design characteristics, the open distal end of the catheter can either get caught on vascular tissue, or can inadvertently get directed into branch vessels, resulting in undesirably extending the time of treatment. It can be desirable to ease the passage through the vasculature by providing the catheter with a removable leader or a bumper tip. Therefore, it would be desirable to provide a catheter that overcomes the aforementioned and other disadvantages.

SUMMARY OF THE INVENTION

The terms "distal" and "proximal" are used in the specification with respect to a position or direction relative to the treating clinician. "Distal" or "distally" are a position distant from or in a direction away from the clinician. "Proximal" and "proximally" are a position near or in a direction toward the clinician.

In a first aspect, the invention is a system for delivering a medical implant to a site within the vasculature of a patient, the system comprising an elongate catheter having a lumen extending therethrough from a proximal end to an open distal end, and wherein at least a distal portion of the lumen is sized to slidably receive the implant. A cap is sealingly affixed to the catheter shaft and spans the open distal end. The cap is elastically distendable into a bulbous shape in response to fluid pressure within the catheter lumen so as to form a bumper tip to safely guide the catheter through the vasculature. The cap is frangible so as to be selectively and controllably ruptured to permit the implant to be ejected through the open distal end of the catheter. The system further includes an inflation device fluidly connected to the catheter lumen for selectively providing fluid pressure therein for distending the cap.

Another aspect of the invention provides a method for delivering a medical implant to a treatment site. The method includes receiving an elongate catheter having a lumen extending therethrough from a proximal end to an open distal end, the open distal end being sealingly covered by a cap and the medical device being slidably disposed within the lumen. The catheter is inserted into the patient's vasculature and the catheter lumen is pressurized to distend the cap into a substantially bulbous shape. With the bulbous bumper tip, the catheter is advanced through the vasculature to the treatment site. Once the treatment site is attained, the cap is ruptured to permit the medical implant to be ejected from the open catheter end.

BRIEF DESCRIPTION OF THE DRAWINGS

The aforementioned and other features and advantages of the invention will become further apparent from the following detailed description of the presently preferred embodiments, read in conjunction with the accompanying drawings, which are not to scale. The detailed description and drawings are merely illustrative of the invention rather than limiting, the scope of the invention being defined by the appended claims and equivalents thereof.

FIGS. 2 and 3 illustrate side and perspective views respectively of a catheter system in accordance with the present invention, shown with the cap undistended;

FIG. 4 illustrates a side view of the catheter system of FIGS. 2 and 3, shown with the cap distended; and FIG. 5 shows a perspective view of the catheter system of FIGS. 2-4, shown with the cap ruptured and an implant partially ejected therethrough.

DETAILED DESCRIPTION OF THE PRESENTLY PREFERRED EMBODIMENTS

Figure 1:
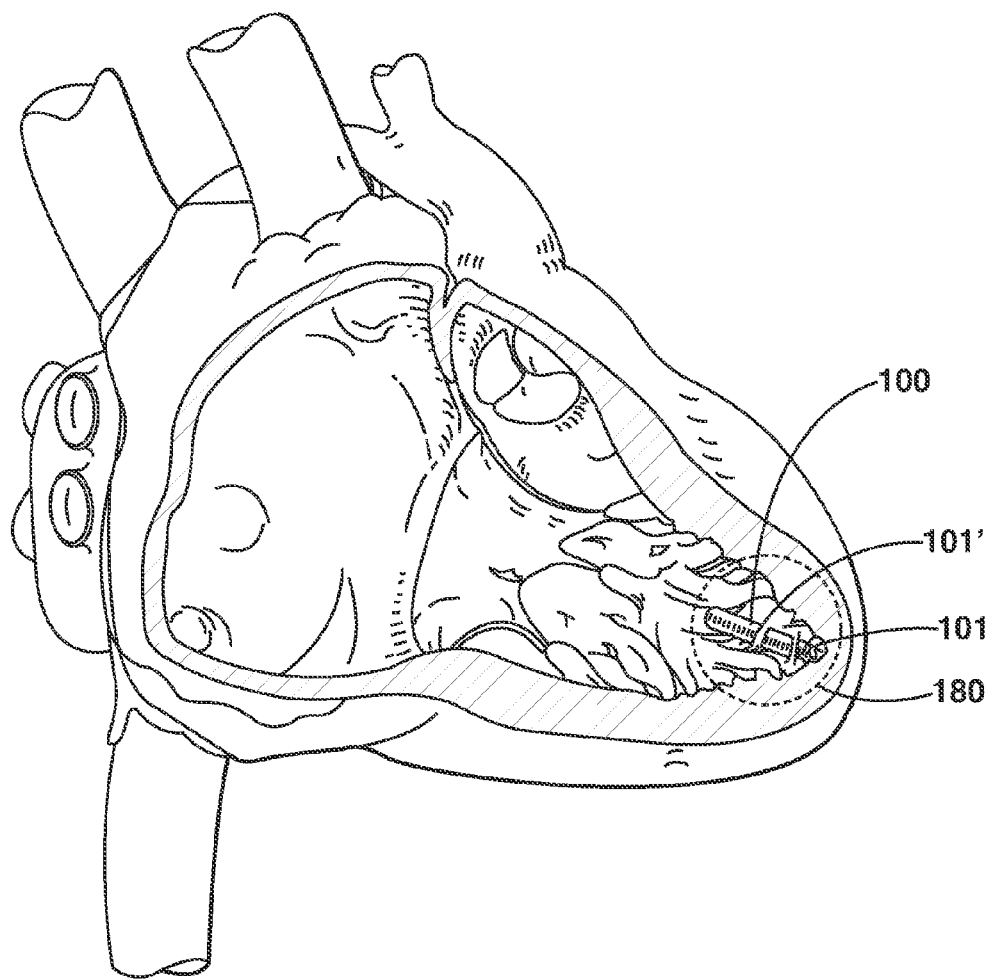
FIG. 1 is a diagram of a human heart with a prior art leadless medical implant implanted within tissue at the apex of the right ventricle.

FIG. 1 illustrates a schematic diagram of a human heart with a prior art leadless cardiac pacemaker 100 implanted within tissue 180 at the apex of the right ventricle. Leadless pacemaker 100 includes a distal screw-like fixation device 101 attached at a distal end thereof and a secondary entanglement fixation structure 101' that radially extends therefrom. Although such leadless pacemakers are small in comparison to conventional pacemakers that are surgically implanted outside of the heart, they are none-the-less rather large in size for delivery by transluminal catheterization, especially because the implants are not collapsible to a smaller delivery configuration and they do not lend themselves to having a through-lumen for delivery over a guidewire.

In minimally invasive procedures for percutaneously delivering a leadless medical implant within the heart, a catheter system is required to carry the implant through the sometimes tortuous vasculature to the treatment site. One aspect of the present invention is a catheter system as illustrated in FIGS. 2 and 3. Catheter 200 includes a lumen 225 extending therethrough from proximal end 230 to open distal end 235. Frangible cap 300 is fixed at the distal end of catheter 200 and includes a planar portion 310 extending across distal open end 235 to form a substantially leak-proof seal at the end of catheter 200. Cap 300 is sufficiently elastic such that fluid pressure selectively supplied to lumen 225 from inflation device 400 via gasket device 500 is capable of causing cap 300 to expand or distend into the substantially bulbous 320 shape illustrated in FIG. 4. Cap 300 is also frangible, i.e. capable of being selectively ruptured, torn, pierced or burst to permit leadless medical implant 100 to be ejected through both catheter open end 235 and cap 300, as illustrated in FIG. 5. Elongate pusher 600 is slidably disposed within catheter lumen 225 and extends from outside of catheter proximal end 230, where it may be manually operated by a clinician, to pusher distal end 610 that may abut and push against implant 100 to eject the implant from catheter 200 and otherwise assist in deployment and implantation of implant 100. Similarly, pusher 600 may be manually secured by the clinician to hold implant 100 in a fixed position within to the patient while catheter 200 is withdrawn proximally over pusher 600 and implant 100 to expose and deploy implant 100.

Catheter 200 and pusher 600 may be made of metal or stiff plastic suitable for insertion into the human body, such as stainless steel, nitinol, high density polyethylene, polyamide, or polyethylene block amide copolymer. Catheter lumen 225 may have a constant diameter from end to end (not shown) for slidably receiving implant 100. Alternatively, only a distal portion 227 of lumen 225 may be sufficiently sized to slidably receive implant 100, as illustrated in FIG. 4. Catheter 200 may be about 50 centimeters to about 150 centimeters long, with a length of about 110 centimeters often being used. The outer diameter of the catheter may range from about 0.110 inches to 0.340 inches.

Cap 300 may comprise one or more elastic polymers including natural or synthetic rubber such as butadiene/acrylonitrile copolymers, copolyesters, ethylene vinylacetate (EVA) polymers, ethylene/acrylic copolymers, ethylene/propylene copolymers, fluorosilicone, latex, polyalkylacrylate polymers, polybutadiene, polybutylene, polyethylene, polyisobutylene, polyisoprene, polyurethane, silicone, styrenebutadiene copolymers, styrene-ethylene/butylene-styrene, thermoset elastomer, thermoplastic elastomer and combinations of the above. Cap 300 may be formed by various methods including casting, compression molding, extrusion blow molding, liquid injection molding, reaction injection molding (RIM), resin transfer molding (RTM), and thermoplastic injection molding. Cap 300 may also be molded of soft foam, solid elastic material, or a combination thereof. Cap 300 may include perforations, grooves or other disruptions that define tear lines (not shown) within the cap. The secure attachment between catheter 200 and cap 300, as by adhesive or melt bonding, prevents their separation, even when cap 300 is distended or selectively ruptured.

Inflation device 400 and gasket device 500 are only shown schematically in FIGS. 2 and 4, as they may be of known construction. For example, inflation device 400 may be a syringe with a screw thread mechanism to adjust and hold pressure, as is common to inflation syringes for inflating catheter balloons used in angioplasty or temporary vessel occlusion. Gasket device 500 may be a passive, non-adjustable seal. Alternatively, gasket device may be an adjustable gasket such as a tuohy borst adapter for permitting pusher 600 to slide therethrough or to selectively seal around pusher 600, thus holding pusher 600 in a fixed position within catheter 200 and preventing pressurized fluid from leaking out of lumen 225.

During use, system 200 with cap 300 in the undistended configuration shown in FIGS. 2 and 3 can be inserted percutaneously into a patient's blood vessel using the Seldinger technique or alternatively, using the surgical cut down approach. Once catheter distal end 235 and cap 300 have entered the blood vessel, with gasket device 500 sealing fluid within lumen 225, inflation device 400 is operated to pressurize lumen 225 via gasket device 500 until cap 300 is expanded into a bulbous distended configuration as illustrated in FIG. 4. Catheter system 200 may then be advanced through the vasculature to the intended implantation site while bulbous cap 300 acts as a bumper to deflect catheter open end 235 off of obstacles and to prevent injury to the various tissues being traversed such as tunica intima and chambers, valves and trabeculae carneae of the heart, as shown in FIG. 1.

Once the distal end of the catheter system has navigated the patient's vasculature to reach the intended implant site, cap 300 can be ruptured. In one example, the pressure applied to lumen 225 by inflation device 400 may be increased until cap 300 bursts. Preferably, the inflation fluid is a sterile liquid such as saline, which may be diluted with x-ray contrast liquid to enhance fluoroscopic guidance, if used.

In another example, the pressure applied to lumen 225 by inflation device 400 may be decreased until cap 300 reverts to the non-distended configuration. Then, implant 100 may be advanced distally using pusher 600 until the distal end of implant 100 penetrates or fractures frangible cap 300 as it passes therethrough, as illustrated in FIG. 5. Alternatively, implant 100 may be held in the desired deployment location by pusher 600 while catheter 200 is withdrawn proximally such that frangible cap 300 splits to expose implant 100 as implant 100 passes through cap 300. Implant 100 may be inserted into catheter 200 only after the catheter distal end has reached the implant site. In such a method, catheter 200 acts like a guiding catheter and implant 100 is pushed all the way through lumen 225 by pusher 600. Alternatively, implant 100 may be preloaded into the distal end of lumen 225 prior to inserting the catheter into the patient. Preloading implant 100 would be necessary in the example shown in FIG. 4, where only distal portion 227 of lumen 225 is sufficiently sized, i.e. large enough in diameter, to receive implant 100.

In the embodiment shown in FIG. 5, as implant 100 exits the distal end 235 of catheter 200, at least planar portion 310 of frangible cap 300 tears into a configuration having one or more deflectable sections 330 such as flaps that swing, stretch, or otherwise move aside, while frangible cap 300 remains integral, i.e. not having any missing parts, and fixed to catheter 200.

While the embodiments of the invention disclosed herein are presently considered to be preferred, various changes and modifications can be made without departing from the spirit and scope of the invention. The scope of the invention is indicated in the appended claims, and all changes and modifications that come within the meaning and range of equivalents are intended to be embraced therein.

What is claimed is:

1. A system for delivering a medical implant to a site within a vasculature of a patient, the system comprising:
   an elongate catheter having a lumen extending therethrough from a proximal end to an open distal end, the catheter being adapted to permit the distal end to be inserted into the vasculature and passed therethrough to the implant site, wherein at least a distal portion of the lumen is sized to slidably receive the implant; and
   a cap sealingly affixed to the catheter and having a planar portion spanning the open distal end, the cap planar portion being elastically distendable into a bulbous shape in response to fluid pressure within the catheter lumen, the bulbous shape being sized to act as a bumper tip for guiding the catheter distal end through the vasculature of the patient;
   wherein the cap is frangible so as to be pierced, fractured or torn to permit the implant to be ejected through the open distal end of the catheter.

2. The system of claim 1 further comprising a medical implant slidably disposed within the catheter lumen.

3. The system of claim 2 further comprising an elongate pusher extending slidably through the catheter lumen and abutting a proximal end of the medical implant, the pusher being capable of ejecting the implant through the open distal end of the catheter.

4. The system of claim 1 further comprising an inflation device fluidly connected to the catheter lumen for selectively providing fluid pressure therein.

5. The system of claim 1 wherein only the distal portion of the lumen is sufficiently sized to slidably receive the implant.

6. The system of claim 5 further comprising a medical implant slidably disposed within the distal portion of the catheter lumen.

* * * * *